US008092396B2

(12) United States Patent
Bagha et al.

(10) Patent No.: US 8,092,396 B2
(45) Date of Patent: Jan. 10, 2012

(54) ELECTRONIC AUSCULTATION DEVICE

(76) Inventors: Merat Bagha, Portland, OR (US);
Arash Tirandaz, Plano, TX (US);
Richard D. Nevin, Portland, OR (US);
Kim Porter Henneman, Portland, OR (US); Steven J. McCoy, Tigard, OR (US); David O. Roethig, Portland, OR (US); I-Chiang Sun, Portland, OR (US)

( * ) Notice: Subject to any disclaimer, the term of this patent is extended or adjusted under 35 U.S.C. 154(b) by 711 days.

(21) Appl. No.: 11/584,236

(22) Filed: Oct. 20, 2006

(65) Prior Publication Data
US 2007/0106179 A1    May 10, 2007

Related U.S. Application Data

(60) Provisional application No. 60/728,568, filed on Oct. 20, 2005.

(51) Int. Cl.
*A61B 5/02*     (2006.01)
*A61B 7/00*     (2006.01)
*A61B 7/04*     (2006.01)

(52) U.S. Cl. ............................ 600/586; 600/528; 381/67

(58) Field of Classification Search .................. 600/300, 600/528, 586; 381/67
See application file for complete search history.

(56) References Cited

U.S. PATENT DOCUMENTS

| | | | |
|---|---|---|---|
| 3,858,005 A | 12/1974 | Marshall et al. | |
| 4,248,241 A | 2/1981 | Tacchi | |
| 4,723,555 A | 2/1988 | Shue | |
| 4,770,189 A | 9/1988 | Shyu | |
| 4,777,961 A | 10/1988 | Saltzman | |
| 4,878,501 A | 11/1989 | Shue | |
| 4,972,841 A | 11/1990 | Iguchi | |
| 5,025,809 A | 6/1991 | Johnson et al. | |
| 5,027,825 A * | 7/1991 | Phelps et al. ................. | 600/528 |
| 5,204,500 A | 4/1993 | Dufresne et al. | |
| 5,206,602 A * | 4/1993 | Baumgartner et al. ........... | 330/9 |
| 5,218,969 A | 6/1993 | Bredesen et al. | |
| 5,360,005 A * | 11/1994 | Wilk .............................. | 600/437 |
| 5,409,010 A * | 4/1995 | Beach et al. .................. | 600/455 |
| 5,663,532 A | 9/1997 | Dieken et al. | |
| 5,717,769 A | 2/1998 | Williams | |
| 5,737,429 A | 4/1998 | Lee | |
| 5,812,678 A | 9/1998 | Scalise et al. | |
| 5,825,895 A | 10/1998 | Grasfield et al. | |
| 5,844,995 A | 12/1998 | Williams | |
| 5,909,495 A | 6/1999 | Andrea | |
| 6,002,777 A | 12/1999 | Grasfield et al. | |
| 6,005,951 A * | 12/1999 | Grasfield et al. ................ | 381/67 |
| 6,171,263 B1 | 1/2001 | Sullivan | |

(Continued)

FOREIGN PATENT DOCUMENTS

DE         10132759          1/2003

(Continued)

*Primary Examiner* — Max Hindenburg
*Assistant Examiner* — Sean Dougherty
(74) *Attorney, Agent, or Firm* — Aboy & Associates, PC

(57) ABSTRACT

An embodiment of an auscultation device can be constructed using electronic components to provide improved acquisition, processing, and communication of sound signals. An input device can be used for detecting sounds, and electrical signals representing the sounds can be processed and transmitted via Bluetooth and/or another form of wireless communication. Such embodiments can employ, at least in part, one or more of several commercially available wireless receiver devices, such as, without limitation, headsets and headphones, mobile phones, PDAs and/or other handheld devices, desktop, laptop, palmtop, and/or tablet computers and/or other computer devices and/or electronic devices.

6 Claims, 15 Drawing Sheets

U.S. PATENT DOCUMENTS

| | | | |
|---|---|---|---|
| 6,244,376 B1 * | 6/2001 | Granzotto | 181/131 |
| 6,344,025 B1 | 2/2002 | Inagaki et al. | |
| 6,358,218 B1 | 3/2002 | Want et al. | |
| 6,396,931 B1 | 5/2002 | Malilay | |
| 6,533,736 B1 | 3/2003 | Moore | |
| 6,540,673 B2 | 4/2003 | Gopinathan et al. | |
| 6,544,198 B2 | 4/2003 | Chong et al. | |
| 6,757,392 B1 | 6/2004 | Granzotto et al. | |
| 6,852,084 B1 * | 2/2005 | Boesen | 600/528 |
| 7,182,733 B2 * | 2/2007 | Sauerland | 600/528 |
| 7,806,226 B2 * | 10/2010 | Drummond et al. | 181/131 |
| 2001/0030077 A1 | 10/2001 | Watson | |
| 2001/0050992 A1 * | 12/2001 | Carman | 381/67 |
| 2002/0071570 A1 | 6/2002 | Cohen et al. | |
| 2002/0085724 A1 * | 7/2002 | Grasfield et al. | 381/67 |
| 2003/0002685 A1 * | 1/2003 | Werblud | 381/67 |
| 2003/0102983 A1 | 6/2003 | Hsieh Hung | |
| 2003/0208130 A1 | 11/2003 | Yotam et al. | |
| 2004/0032957 A1 * | 2/2004 | Mansy et al. | 381/67 |
| 2004/0037429 A1 * | 2/2004 | Candioty | 381/67 |
| 2004/0068194 A1 * | 4/2004 | Johnson et al. | 600/508 |
| 2004/0076303 A1 | 4/2004 | Vyshedskiy et al. | |
| 2004/0092846 A1 | 5/2004 | Watrous | |
| 2004/0096069 A1 * | 5/2004 | Chien | 381/67 |
| 2004/0157612 A1 | 8/2004 | Kim | |
| 2004/0220487 A1 | 11/2004 | Vyshedskiy et al. | |
| 2004/0220488 A1 | 11/2004 | Vyshedskiy et al. | |
| 2004/0223621 A1 | 11/2004 | Orten | |
| 2004/0225476 A1 | 11/2004 | Tien | |
| 2004/0228494 A1 * | 11/2004 | Smith | 381/67 |
| 2004/0249298 A1 | 12/2004 | Selevan | |
| 2005/0043642 A1 * | 2/2005 | Sauerland | 600/528 |
| 2005/0070811 A1 | 3/2005 | Crowley | |
| 2005/0074130 A1 | 4/2005 | Brummel et al. | |
| 2005/0083194 A1 | 4/2005 | Shen | |
| 2005/0090755 A1 | 4/2005 | Guion et al. | |
| 2005/0101843 A1 | 5/2005 | Quinn et al. | |
| 2005/0119584 A1 | 6/2005 | Carter | |
| 2005/0148883 A1 * | 7/2005 | Boesen | 600/485 |
| 2005/0157887 A1 | 7/2005 | Kim | |
| 2005/0157888 A1 | 7/2005 | Yang | |
| 2005/0163337 A1 * | 7/2005 | Ruegg | 381/370 |
| 2005/0165310 A1 | 7/2005 | Bindefeld | |
| 2005/0203349 A1 | 9/2005 | Nanikashvili | |
| 2006/0047215 A1 * | 3/2006 | Newman et al. | 600/513 |
| 2006/0056641 A1 * | 3/2006 | Nadjar et al. | 381/67 |
| 2006/0158344 A1 * | 7/2006 | Bambini et al. | 340/825.69 |
| 2006/0285696 A1 * | 12/2006 | Houtsma | 381/67 |
| 2007/0049838 A1 * | 3/2007 | Sauerland | 600/528 |
| 2007/0058818 A1 * | 3/2007 | Yoshimine | 381/67 |
| 2007/0106179 A1 * | 5/2007 | Bagha et al. | 600/586 |
| 2008/0093157 A1 * | 4/2008 | Drummond et al. | 181/131 |

FOREIGN PATENT DOCUMENTS

| | | |
|---|---|---|
| FR | 2768323 | 3/1999 |
| JP | 53149352 | 12/1978 |
| JP | 2004081250 | 3/2004 |
| JP | 2004261264 | 9/2004 |

* cited by examiner

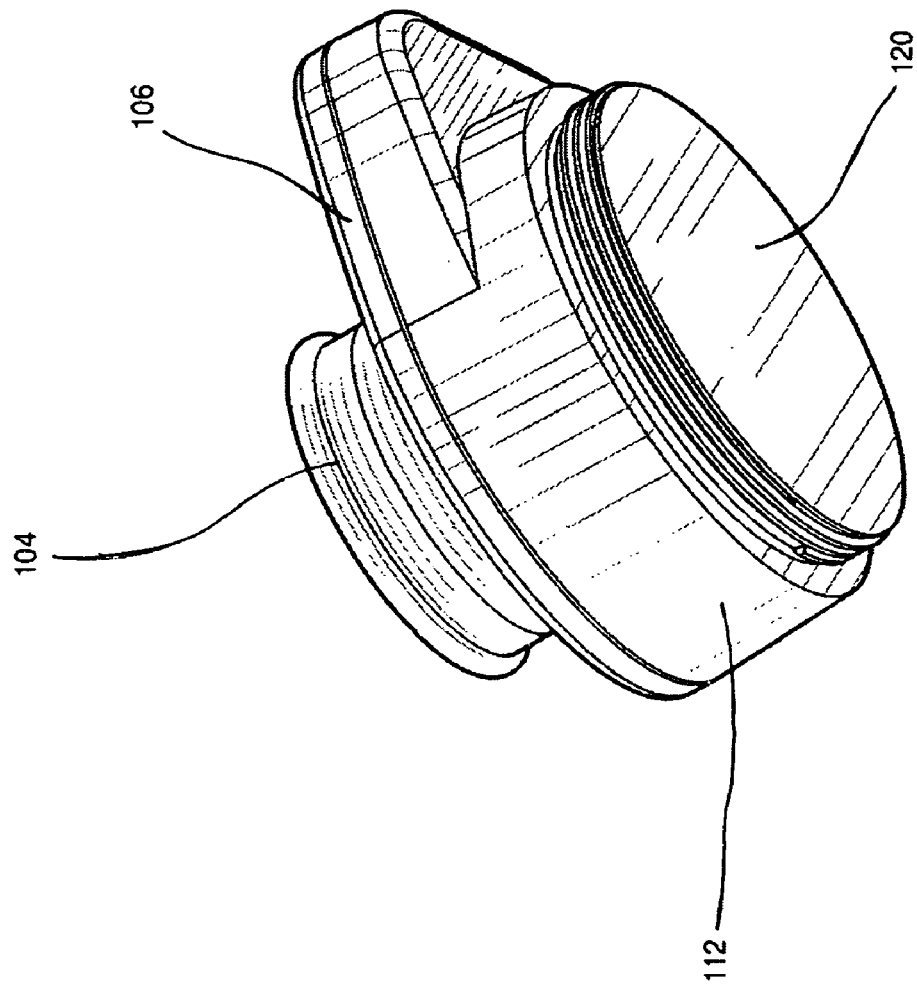

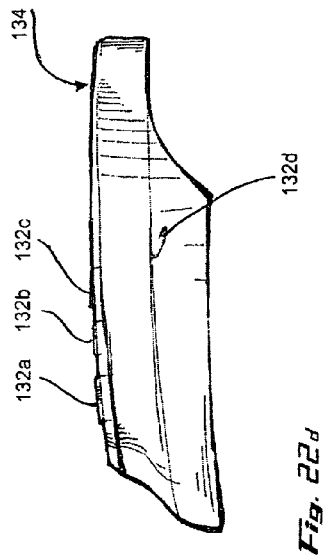
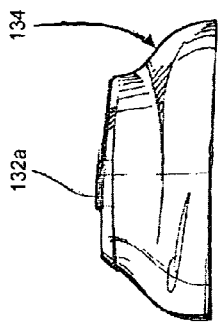
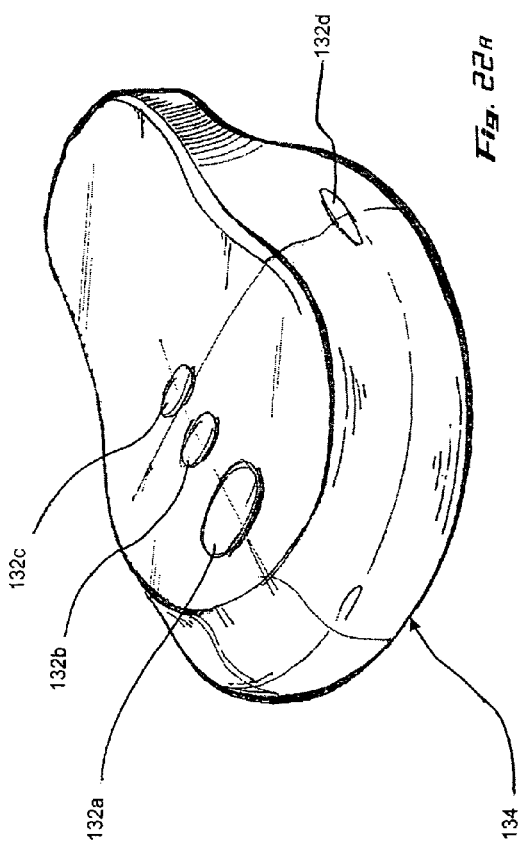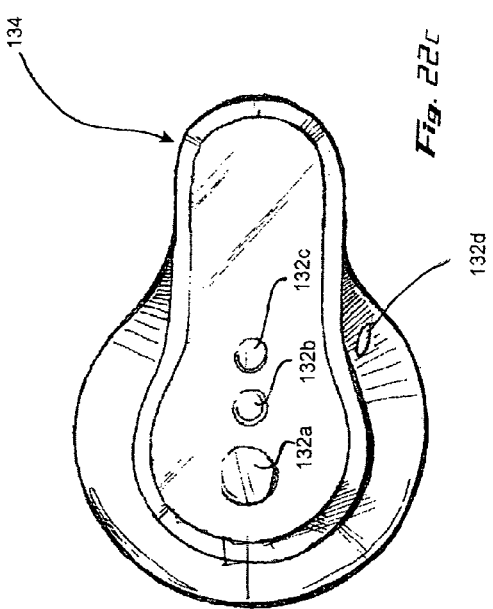

ELECTRONIC AUSCULTATION DEVICE

RELATED APPLICATIONS

This application claims priority from, and is a nonprovisional of, U.S. Provisional Patent Application No. 60/728,568, filed Oct. 20, 2005, which is hereby incorporated by reference in its entirety.

COPYRIGHT NOTICE

© 2006 Tiba Medical, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d), (e).

TECHNICAL FIELD

Embodiments consistent with the present application relate to one or more methods, apparatuses, and/or systems for medical examination, testing, and/or diagnosis.

BACKGROUND

Auscultation techniques are useful for medical examination, testing, and diagnosis. Typically, auscultation involves a qualified medical practitioner listening to the internal sounds of a subject's body, usually using a stethoscope. Auscultation is normally performed to examine biological systems, such as the cardiovascular, respiratory, and/or gastrointestinal systems.

Auscultation is a skill that requires substantial clinical experience, and an environment that permits clear hearing. Heart sounds, for example, can sound rather faint through an acoustic stethoscope. Tubes used to transmit acoustic sounds through traditional stethoscopes can create extraneous noise when the tubes rub against hands, body, or clothing, etc. Additionally, traditional stethoscopes poorly accommodate those with moderate to severe hearing loss, or those who work in noisy environments (e.g., emergency rooms, helicopters, etc.).

Another problem with many existing auscultation devices is that they are constructed of a metallic material. Metallic surfaces can be cold to the touch when placed against the skin of a subject. They also can show poor resistance to moisture, thus being susceptible to water damage.

SUMMARY

Embodiments of an auscultation device can be constructed employing one or more electronic components to facilitate electrical processing and/or transmission of sound, including, without limitation, performing signal enhancement and/or data communication functions. One embodiment of an auscultation device can transmit sound data wirelessly. Device embodiments can be constructed with an ergonomically sized and shaped casing that is comfortable for an operator to use. Similarly, one or more contact surfaces on the casing, which come into contact with the subject, can be constructed of a material that is easy-to-clean, waterproof or water resistant, and not cold to the touch. a casing having a contact surface to be placed in contact with a subject.

An auscultation device embodiment including an input device for detecting sound from the subject. The sound is converted into an electrical signal, and a controller can be employed for processing the electrical signal. Controller embodiments can employ digital signal processors and/or other processing logic to facilitate amplification, diagnosis, and/or selective filtering of electrical signals representing detected sounds. Embodiments can transmit a processed signal via an integrated wireless communication interface to a remote receiver. Numerous commercially available wireless receivers can be used as a remote receiver, such as, without limitation, headsets and headphones, mobile phones, PDAs and/or other handheld devices, desktop, laptop, palmtop, and/or tablet computers and/or other computer devices and/or electronic devices.

BRIEF DESCRIPTION OF THE DRAWINGS

FIG. 3 illustrates sample electronic component embodiments comprising an auscultation device consistent with the claimed subject matter.

FIGS. 9-21 illustrate examples of relative interrelation and/or placement of the sample electronic component embodiments of FIG. 3 to assemble the embodiment of the auscultation device represented in FIG. 4.

FIGS. 22A-22D depict an alternative embodiment of a chest piece consistent with the claimed subject matter.

DETAILED DESCRIPTION

Figure 2:
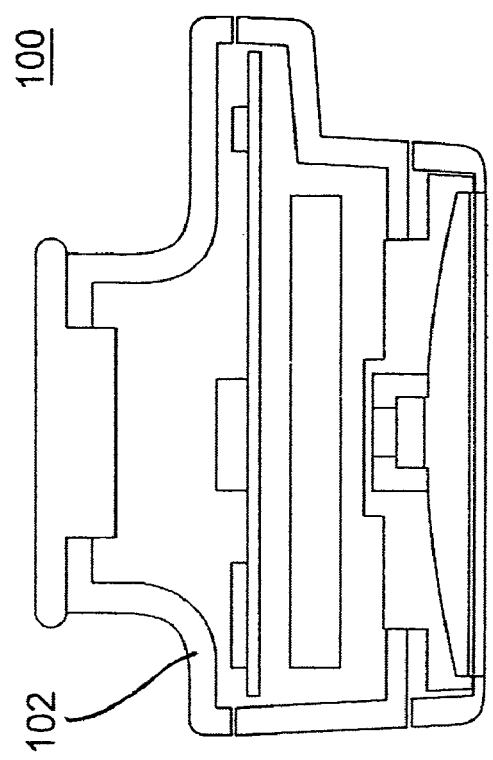
FIG. 2 depicts the chest piece embodiment of FIG. 1 from a side view.

In one embodiment, presented herein for illustrative purposes and without limitation, the claimed subject matter can encompass an auscultation device, such a stethoscope, as but one example, to be used by physicians or other professionals to detect and/or monitor biological sounds of the body (human, animal, etc.) such as the heart or the lung. In one embodiment, for example, an auscultation device can utilize Bluetooth® wireless technology to reduce or eliminate use of the tube that connects the chest piece to the ear piece in traditional auscultation devices. Present embodiments can offer compatibility with various wireless protocols, including Bluetooth 1.2 and/or 2.0, and/or later specification standards, as but a few examples. The claimed subject matter is not limited in this regard, however, as alternative or additional wireless standards can also be employed consistent with the claimed subject matter.

Embodiments can function with commercially available Bluetooth and/or other applicable wireless receivers including, without limitation, audio devices such as headsets and headphones, mobile phones, PDAs and/or other handheld devices, desktop, laptop, palmtop, and/or tablet computers and/or other computer devices and/or electronic devices, as but a few examples. The claimed subject matter, however, is not limited to the illustrative characteristics described with respect to these embodiments. Alternative embodiments can employ additional or alternative wireless receiver devices, standards, and/or technologies, now known or later developed, consistent with the claimed subject matter.

Wireless transmissions can be substantially secure and reliable in various locations and/or environments, such as clinics, hospitals, and/or other settings where numerous types of equipment or alternate sources of potential signal interference can be present. In one example, an embodiment can be used by a doctor as part of a routine medical examination in an examination room of a medical office, as well as other potential locations. In another example, an embodiment can be used in a surgical room, or other location, as a pre-tracheal, precordial, and/or esophageal stethoscope or auscultation device, which can be used by an anesthesiologist to monitor for blocked air passages in the patient by listening to the patient's breathing sounds. Eliminating the tube used in traditional devices can allow the anesthesiologist to be free of the tube connecting them and the patient, while still remaining in the room and attending to the patient during the procedure/operation. However, in certain implementations or for select users, the look and feel of a more traditional stethoscope may still be considered desirable. In such cases one or more embodiments can offer a user wireless transmission and additionally or alternatively include the ability to transmit signals via an interface to, as one example, a wired headset through one or more audio connections. Such audio connections can include, for example, a substantially standard 3.5 mm audio jack, or an integrated electronic earpiece, as but two examples presented for illustrative purposes and not by way of limitation. Additional and/or alternative sound or data transmission mechanisms could also be employed. Embodiments that allow the user to choose wired and/or wireless communications methods can offer increased flexibility.

Embodiments employing electronic technology can also include signal processing capabilities that can enable amplification, diagnosis, and/or filtering of detected sounds, as but a few examples. By enabling signal processing, embodiments can, for example, help accommodate or assist those with moderate hearing-loss or those who work in noisy environments (e.g., emergency rooms, helicopters, etc.). Such embodiments can help produce improved sound quality (e.g., sound quality that is sharper, crisper, and clearer, etc.), thus enabling better diagnosis of a patient's condition.

Figure 1:
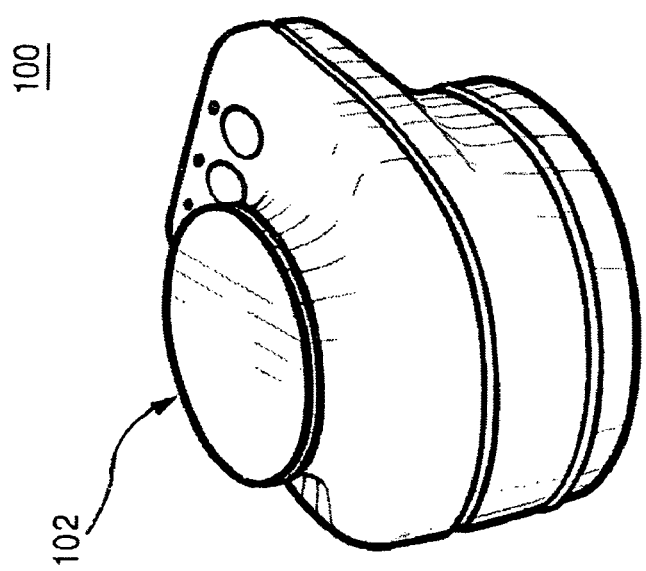
FIG. 1 depicts one embodiment of an auscultation device implemented as an electronic chest piece embodiment consistent with the claimed subject matter.
Figure 1:
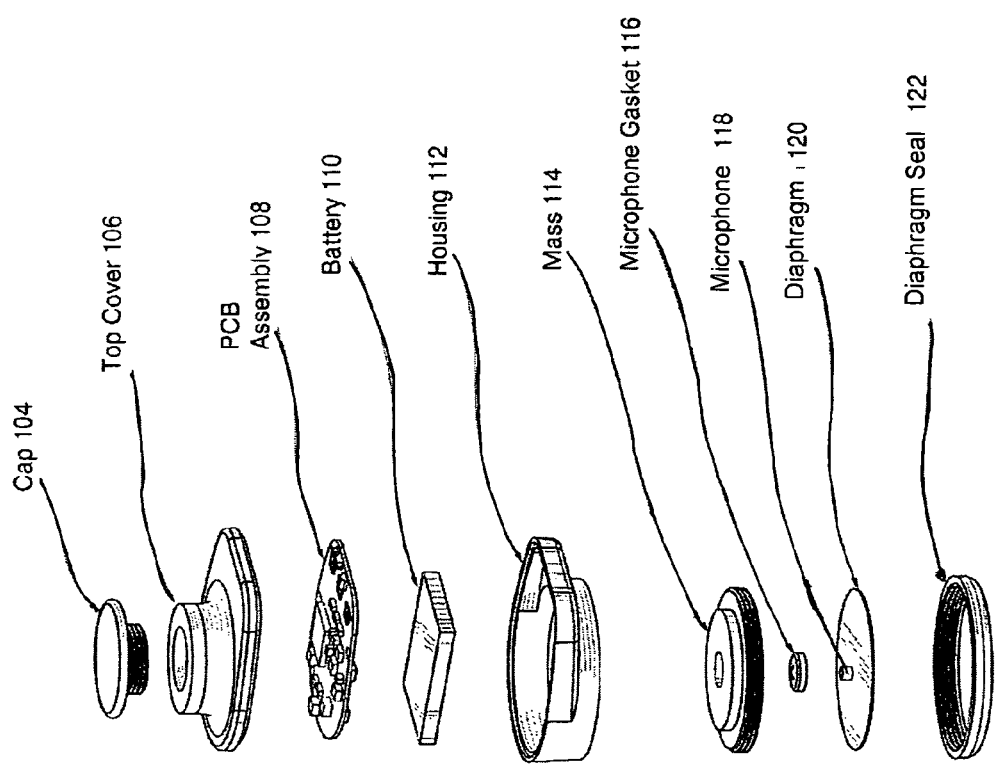

A device consistent with one embodiment of the present technology may include, at least in part, a chest piece with a built-in microphone and wireless transmitter. FIG. 1 and FIG. 2 illustrate one embodiment of a chest piece consistent with the claimed subject matter. Such a chest piece can include the ability to interface with a Bluetooth wireless receiver such as an earpiece, headset, headphone, PC, PDA, tablet computer, and/or other computer and/or electronic device, among others. Embodiments offering flexibility in the type and/or style of receiver employed can present distinct advantages to users. For example, a user that has an in-the-ear hearing aid can choose to use a wireless over-the-ear style headset as the receiver, thus improving comfort.

Presently disclosed embodiments can achieve improved sound amplification while also including a chest piece or other component that can support both bell and diaphragm modes (e.g., enabling heart and lung examination, etc.). For example, and without limitation, one embodiment can support frequency ranges such as 20-200 Hz for bell mode operation, 100-500 Hz for diaphragm mode operation, and/or 20-1000 Hz for a combined bell/diaphragm mode operation.

One embodiment consistent with the claimed subject matter can offer improved sound transmission. For example, an embodiment can offer improved sound amplification. For example, embodiments can be provided that can produce signals enhanced to approximately 40 times or 50 times that of traditional stethoscopes. These magnitudes of enhancement, however, are presented for illustration only, and not by way of limitation. The claimed subject matter is not limited in this regard. Alternate amplification parameters can be selected to satisfy the intended use for the embodiment and alternate embodiments can achieve alternate levels and/or ranges of sound amplification. An embodiment providing electronic amplification can aid a user in examining a patient such as, for example, an obese individual having a lot of fatty tissue, which can make listening to heart and lung sounds difficult. Embodiments of the present technology can also allow for the filtering of ambient sounds and artifacts such as hand motions and/or contact with body hair. In one example, which is presented for illustrative purposes and not by way of limitation, an embodiment can exhibit signal-to-noise consistent with one or more specified ranges (e.g., greater than 88 decibels, etc.). However, alternate embodiments can exhibit alternate signal-to-noise ratios and/or varying operable ranges.

For illustrative purposes and for facilitating disclosure, reference will be made herein to the embodiments illustrated in the drawing figures. It should be noted however, that these embodiments and their respective component embodiments are presented for illustrative purposes only, and not by way of limitation. Additional and/or alternative embodiments and/or component embodiments can also be employed consistent with the claimed subject matter. Beginning the discussion with reference to FIGS. 1 & 2, a chest piece 100 (as well as any separate receiver component, which is not pictured) can include a casing 102 that can be sized, shaped, formed, and/or constructed so as to be easily and/or comfortably grasped and manipulated by an operator using one hand and placed against a subject during use.

Figure 4:
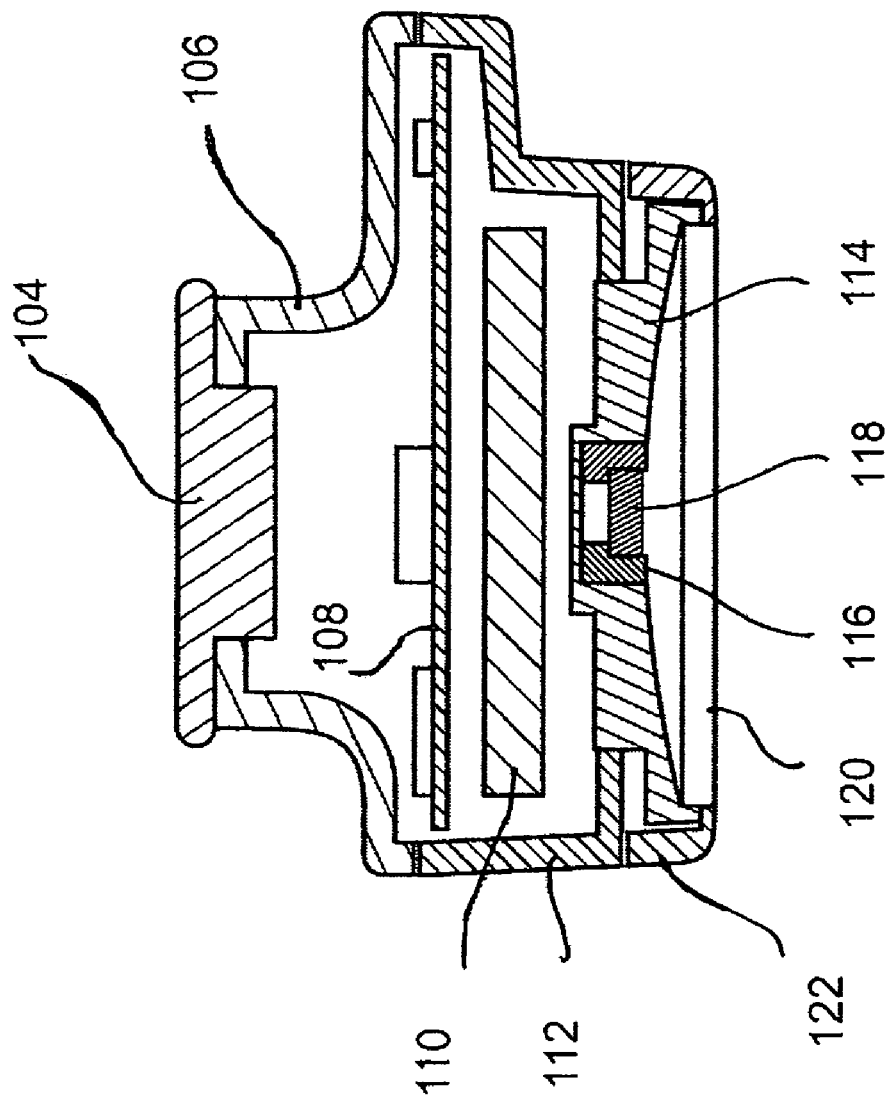
FIG. 4 illustrates the electronic component embodiments of FIG. 3 in an assembled sate.

For illustrative purposes, and not by way of limitation, FIG. 3 illustrates a few examples of electronic component embodiments that can be used to assemble an auscultation device consistent with the claimed subject matter. For additional illustration, the electronic component embodiments illustrated in FIG. 3 are also illustrated in FIG. 4 as a completed assembly. With detailed reference to FIG. 3, examples of electronic component embodiments can include a cap 104, a top cover 106, a printed circuit board (PCB) assembly 108, a battery and/or alternative power source 110, a housing 112, a mass 114, a microphone gasket 116, a microphone 118, a diaphragm 120, and a diaphragm seal 122. Of course, those skilled in the relevant art will appreciate that fewer, additional, and/or alternative electronic component embodiments could be used, depending at least in part on the desired implementation, while still remaining consistent with the claimed subject matter. FIG. 4 illustrates, in transparent side view, one embodiment of an assembly of the component embodiments that are illustrated in exploded view in FIG. 3.

Figure 6:
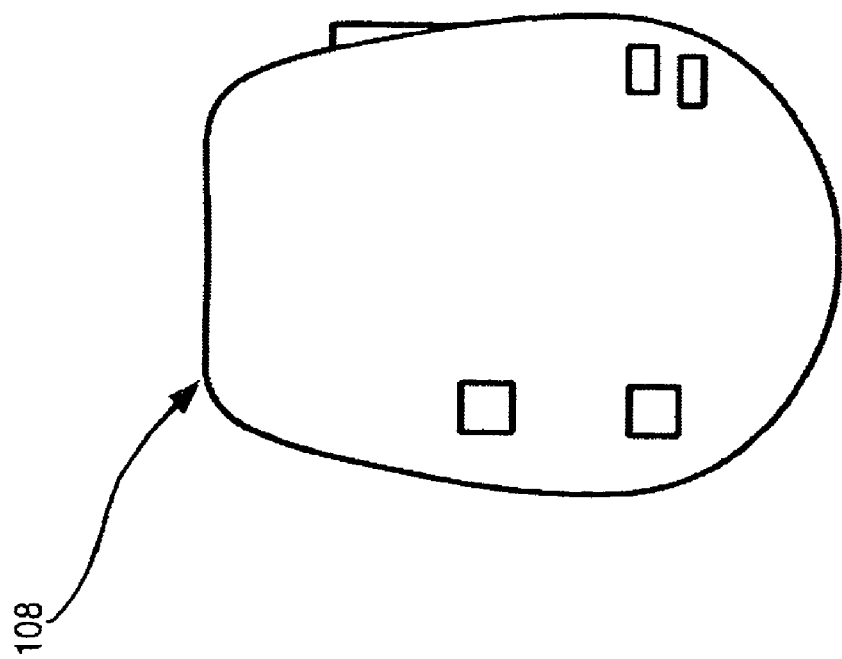
FIGS. 5-6 illustrate an embodiment of a printed circuit board (PCB) layout for use in an auscultation device consistent with the claimed subject matter.
Figure 5:
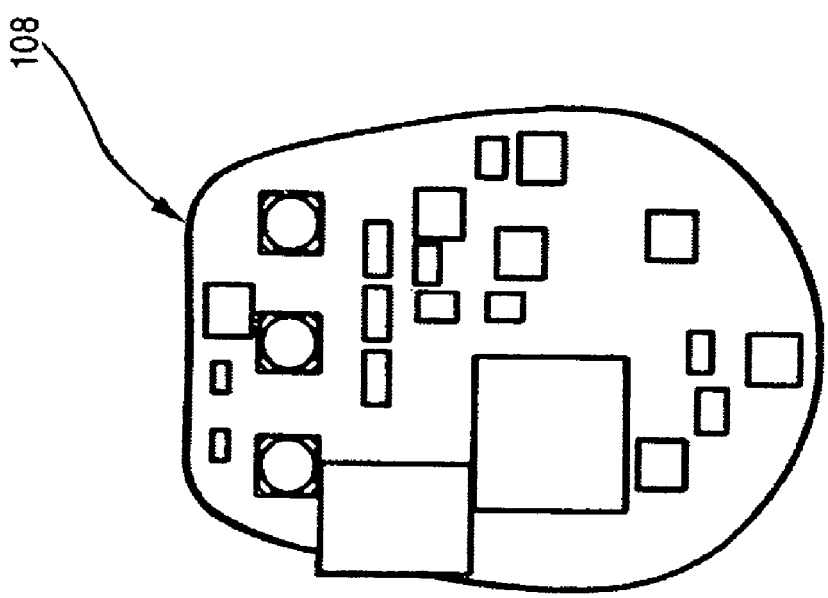
Figure 8:
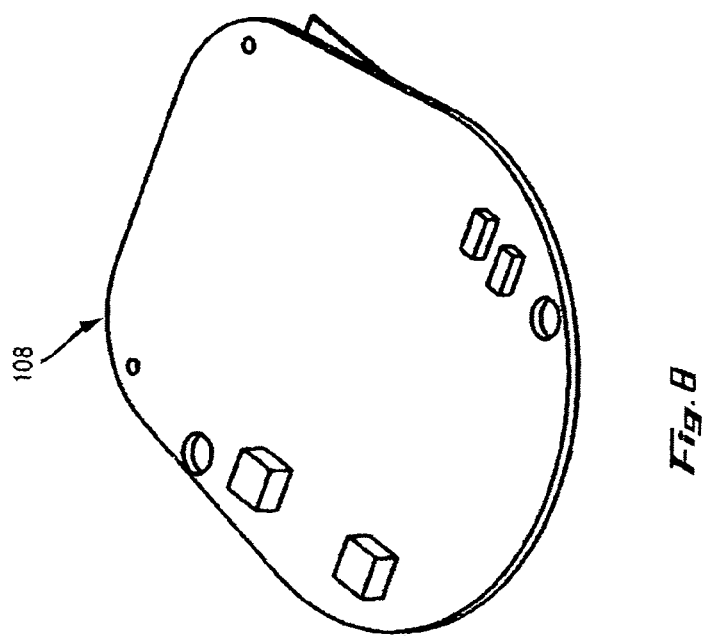
FIGS. 7-8 illustrate one embodiment of the PCB layout of FIGS. 5-6 with electronic components attached.
Figure 7:
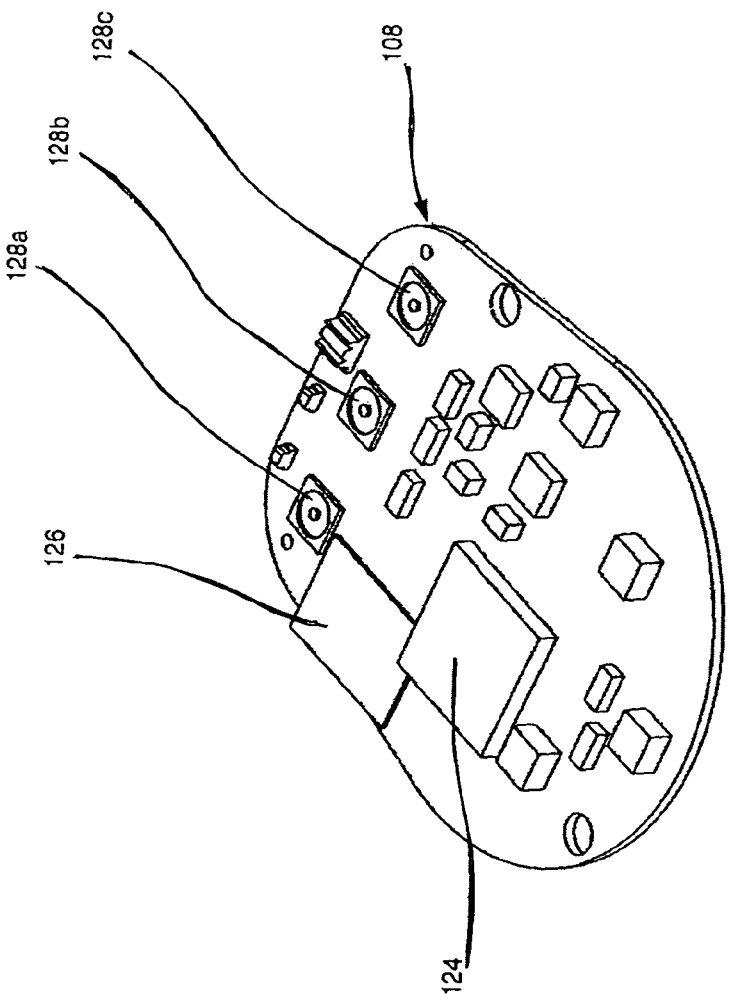

FIGS. 5 and 6 illustrate an embodiment of a PCB assembly 108, showing a sample PCB and PCB component layout from a top and bottom view, respectively. FIGS. 6 and 7 also respectively present a top and bottom view of a PCB assembly 108. FIGS. 6 and 7 also illustrate a few examples of electronic components that can be included for a PCB assembly 108. For example, component embodiments can include a controller embodiment 124, a wireless interface embodiment 126, and LEDs and/or other display embodiments 128a-128c, to illustrate just a few examples.

Figure 10:
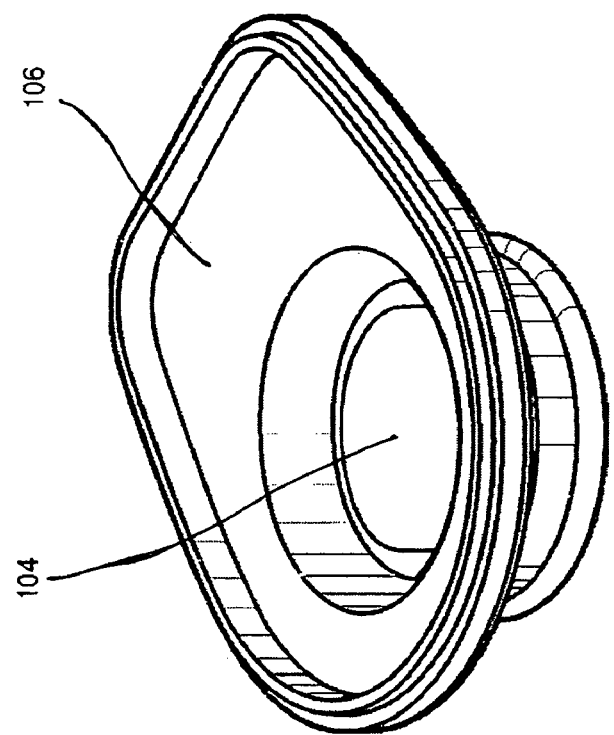
Figure 9:
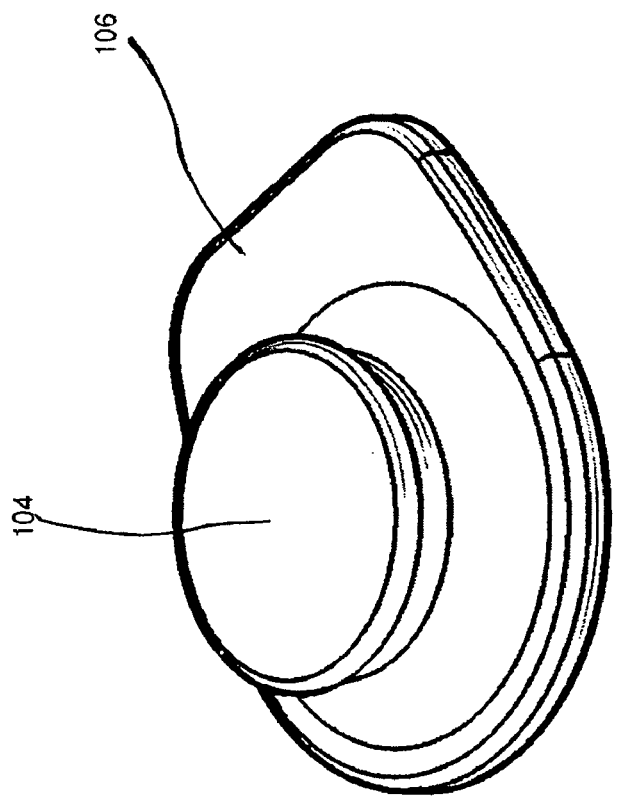
Figure 12:
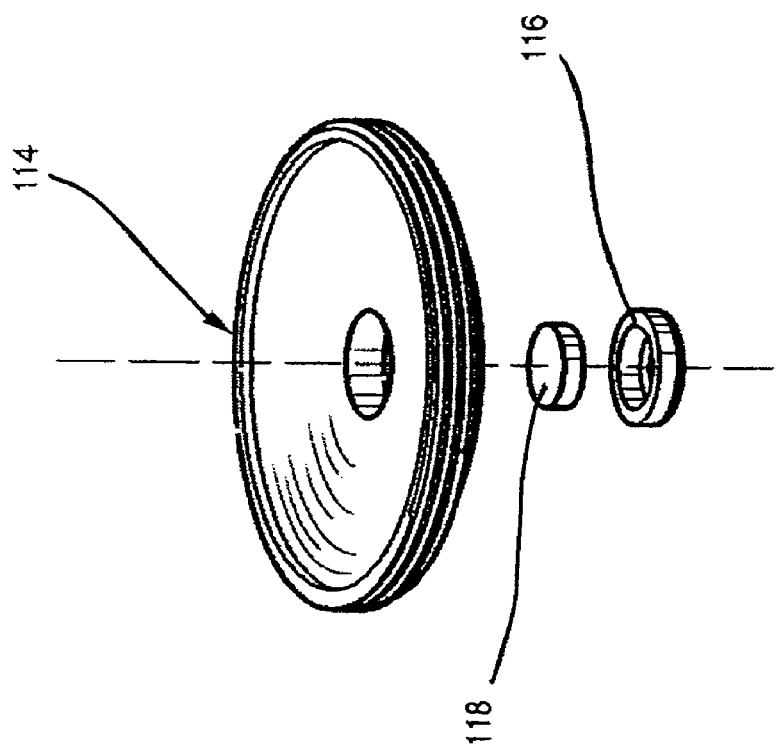
Figure 11:
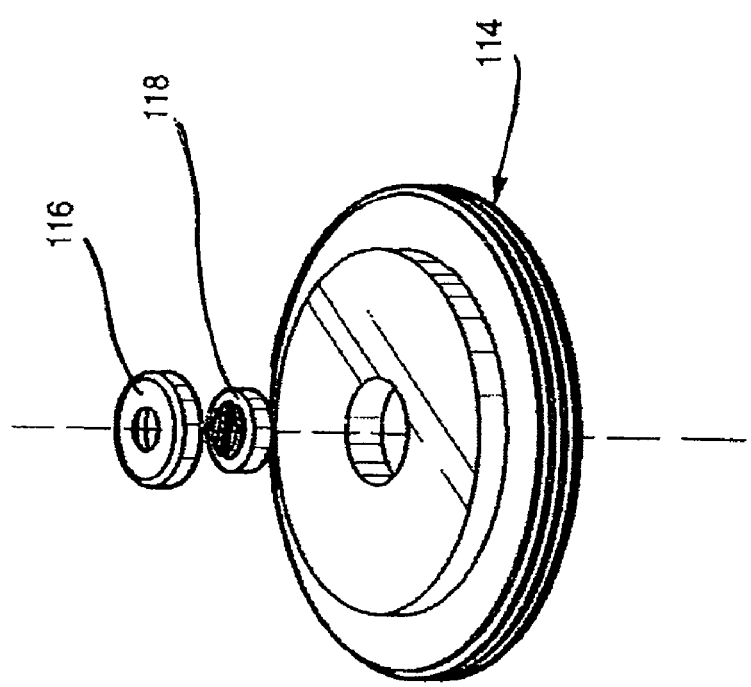
Figure 14:
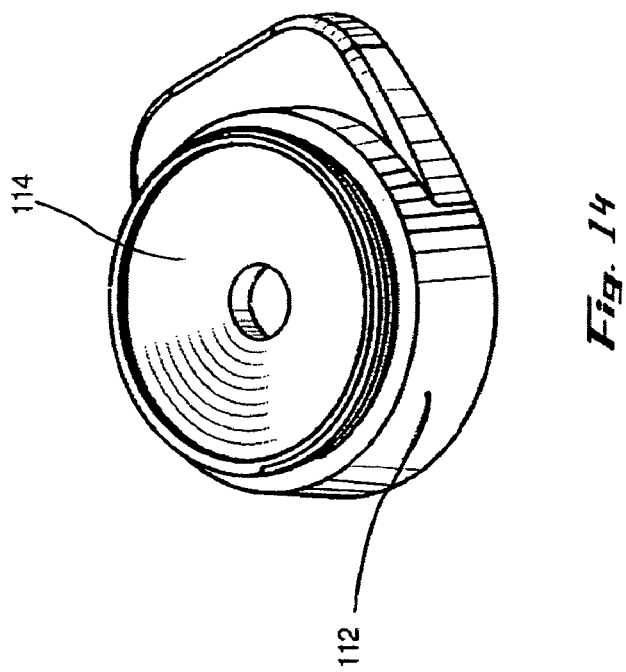
Figure 13:
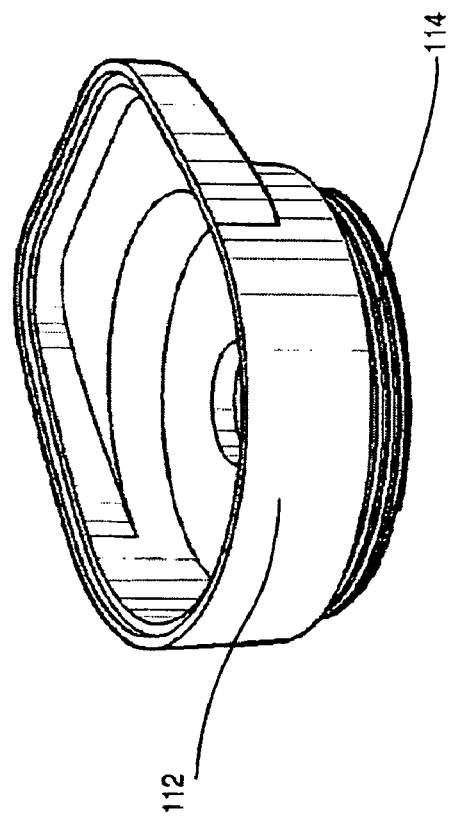
Figure 16:
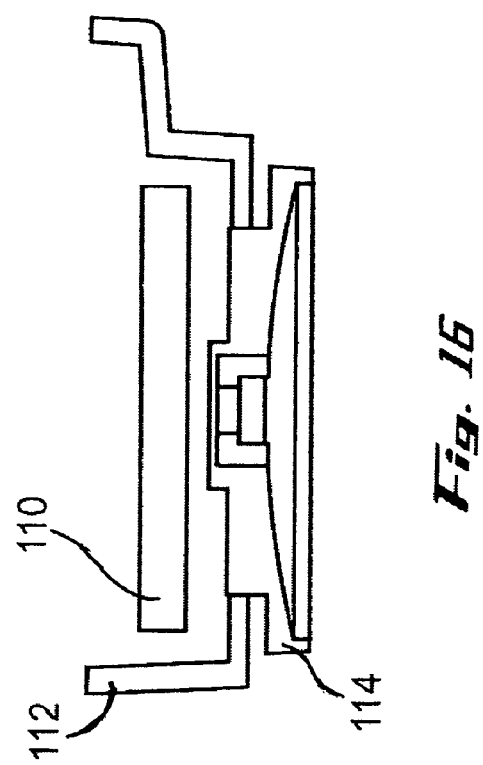
Figure 15:
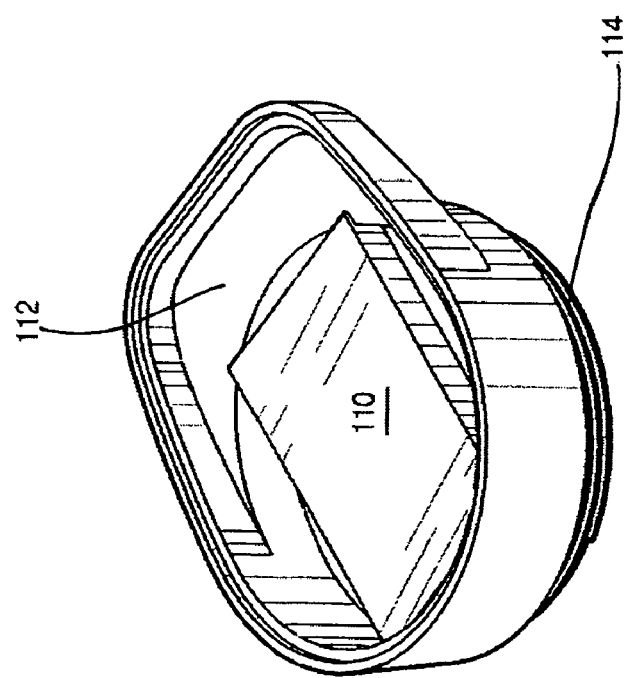

As additional illustration of one embodiment consistent with the claimed subject matter, FIGS. 9-21 illustrate, as but one example, a relative interrelation and/or placement of the electronic component embodiments illustrated in FIG. 3, as they can be used to assemble the embodiment of the auscultation device illustrated in FIG. 4. For example, FIG. 9 and FIG. 10 illustrate one example of an assembly of a cap embodiment 104 and a top cover embodiment 106. Cap embodiment 104 can be bonded, welded, painted-on and/or otherwise affixed (substantially temporarily or substantially permanently) to top cover embodiment 106. FIG. 11 and FIG. 12 illustrate one example of an assembly of a mass embodiment 114, a microphone gasket embodiment 116, and a microphone embodiment 118. As illustrated, microphone embodiment 118 can be inserted into gasket embodiment 116, which in turn can be inserted into mass embodiment 114. Similarly, FIG. 13 and FIG. 14 illustrate the insertion of mass embodiment 114 into a housing embodiment 112 as part of the assembly embodiment. As illustrated in FIG. 15 and FIG. 16, a power source embodiment 110 can be provisioned within housing embodiment 112. In one assembly embodiment, power source embodiment 110 can be provisioned substantially securely within housing embodiment 112 by using ribs, protrusions, or insets integrated into the formation of housing embodiment 112.

Figure 17:
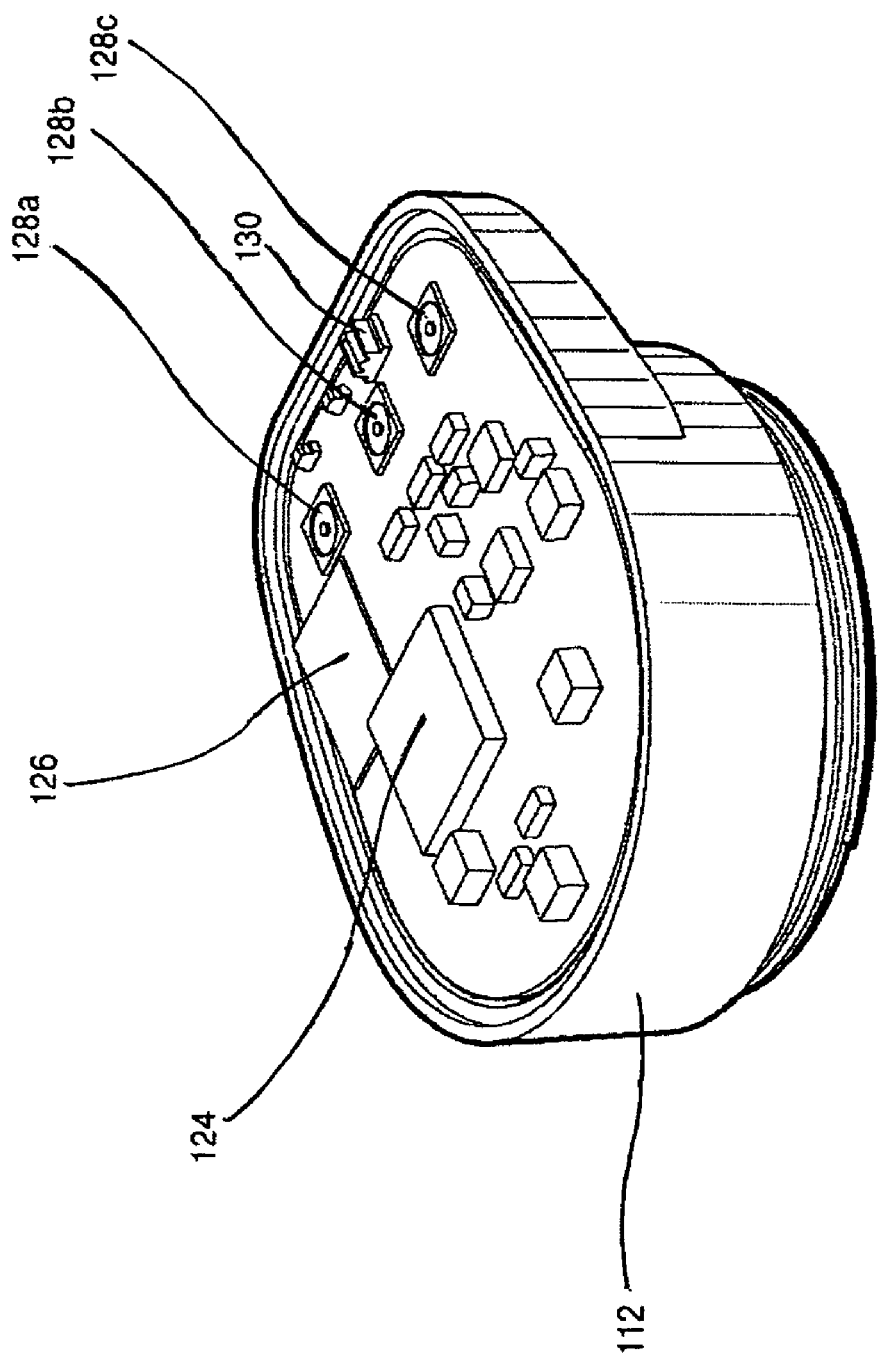
Figure 19:
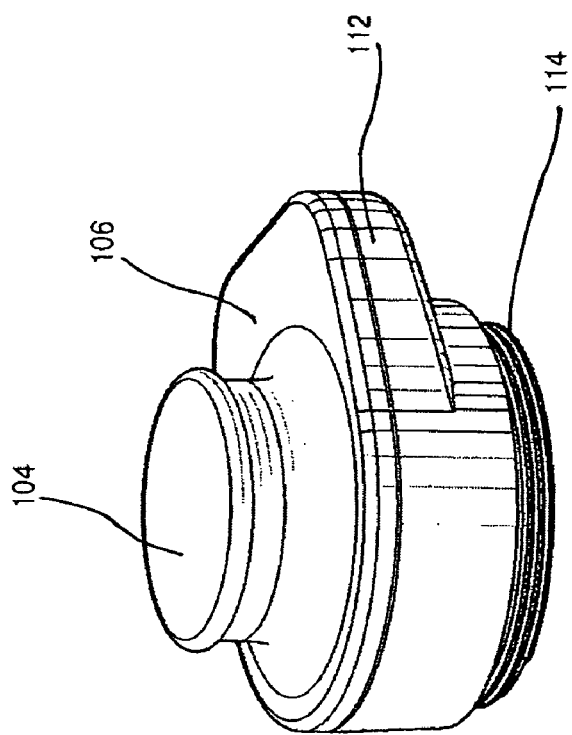
Figure 18:
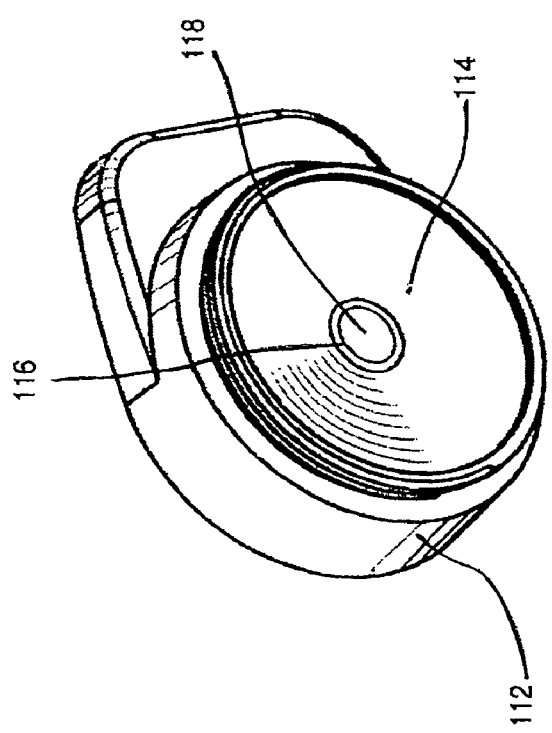
Figure 21:
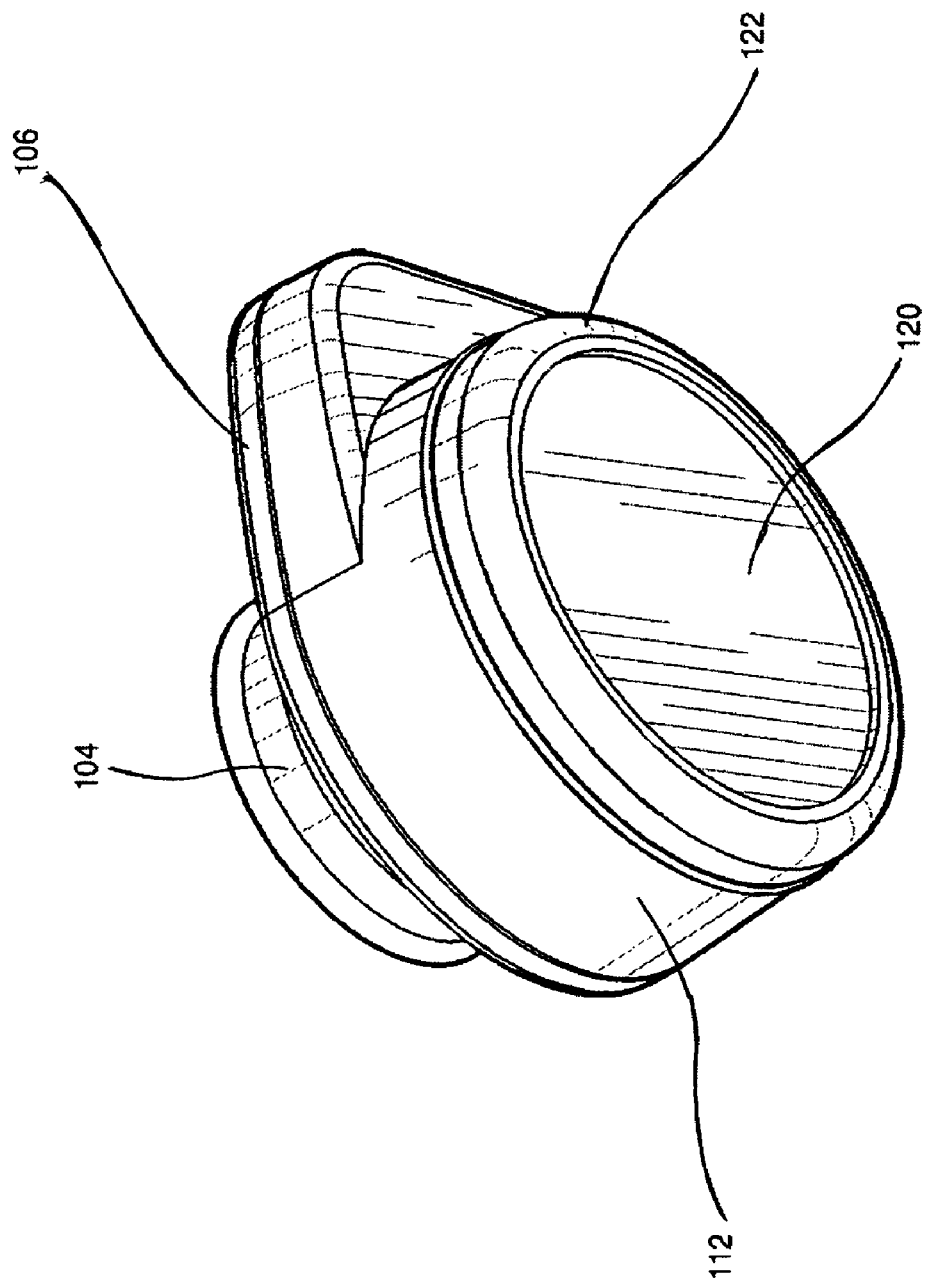

Continuing with the illustrated example of a chest piece assembly embodiment, FIG. 17 illustrates a PCB assembly embodiment 108 provisioned within housing 112. As illustrated in FIG. 7, PCB assembly 108 of FIG. 17 also depicts, for illustration and not as a limitation, a controller embodiment 124, a wireless interface embodiment 126, display embodiments 128a-128c, as well as an embodiment of a user input control 130. FIG. 18 and FIG. 19 illustrate an assembly embodiment with a cap embodiment 104 and a top cover embodiment 106 being coupled to housing embodiment 112. Such components can be coupled via welding, screw thread mechanisms, and/or other means, depending, at least in part, on whether it is desired that the assembly be substantially permanently or substantially temporarily assembled. FIG. 20 illustrates one example of a diaphragm embodiment 120 being provisioned relative to housing embodiment 112. Additionally, FIG. 21 presents one example of a diaphragm seal embodiment 122 being coupled to housing embodiment 112 to substantially securely maintain the position of diaphragm embodiment 120 within housing embodiment 112. Diaphragm seal embodiment 122 can be coupled via threaded attachment to housing embodiment 112, and/or affixed via other methods know to those skilled in the relevant arts.

Chest piece embodiments consistent with the claimed subject matter can employ a battery power source and exhibit an overall ergonomic construction with one or more aspects that are designed to be compact, light-weight, rugged, and/or durable. The chest piece can be accompanied by an optional cradle that can provide convenient storage and/or a power source or interface for recharging rechargeable batteries. An embodiment can also include a headphone or other receiver. In one example, a receiver embodiment can be provided that can cooperate functionally with the chest piece. A receiver embodiment can be provided substantially to match, approximate, and/or complement the ergonomics, design elements, and/or other aspects of the chest piece. Batteries used in embodiments can be selected to provide a sufficient operating life to meet expected operating requirements of the user (e.g., batteries can provide a sufficient charge for 18 hours of continuous operation, etc.). One embodiment can also include an auto-off function to preserve battery life when the device is not in use for some predefined amount of time (e.g., one, two, three, minutes, or other time intervals, etc.). Embodiments can use commercially available rechargeable batteries which can be easily changed and/or recharged via intelligent and rapid charging. Embodiments using rechargeable batteries can support sufficient charge/recharge cycles as determined per user requirements (e.g., batteries can be charged/recharged for a year or more, etc.). Batteries can also be replaced after their effective life, but a battery compartment cover of the embodiment can be securely held in place so that it will resist detachment from the device if the device is dropped. One embodiment of a battery charger can operate in the range of 90-240 VAC, 50/60 Hz, for example, although alternate/additional operating ranges can be exhibited/enabled for operation in various geographic locations and/or environments.

An embodiment's chest piece electronics may encompass a printed circuit board having programmable memory that will enable a variety of additional or alternate functionality. For example, the chest piece may include onboard memory for recording and storing measurements. The chest piece may also include a built-in speaker or audio jack to enable the playing of sounds either in real-time, or via playback from memory. When incorporated with a loudspeaker, such as a Bluetooth-based loudspeaker, as but one example, embodiments can broadcast detected sounds for multiple individuals to hear. Such embodiments can be useful, in one example, in environments where multiple people can be present, such as multiple medical practitioners, colleagues, family members, observing students, etc. Current or stored readings (which can be stored in a memory module onboard the PCB) can also be transmitted via wired or wireless connection to a computer or other receiver device for recording and/or analysis. Wireless communications can also take advantage of one or more networks to transmit examination information over potentially long distances. For example, one embodiment can include a chest piece that can wirelessly transmit examination information to a Bluetooth-enabled mobile phone, which in turn can transmit the received signal over one or more wireless phone networks to an end user at a remote location.

The chest piece may also wirelessly transmit readings, or include an LED, LCD, or other onboard display, for displaying pulse rate information or QRS heart rhythm information, measured using two or three ECG leads, which may be built into the chest piece, for example. Such displays can present information in a textual, graphical, symbolic, and/or other form. An embodiment with an on-board display and/or one or more controls, such as buttons, for example, can be designed so that the displays and/or controls can be viewed and accessed at a variety of angles and in varying light conditions, ranging from high to low levels of direct or indirect, natural or artificial light.

Embodiments can be constructed to meet pertinent safety, environmental, and/or regulatory standards (including those promulgated by the United States FDA, FCC, and/or IEC, as well as the European CE Mark authorities or other agencies/regulatory bodies) that can govern the intended use of an embodiment. Embodiments consistent with the claimed subject matter can also exhibit a variety of characteristics that can offer operating advantages for the intended user or patient. For example, one embodiment, which is described by way of illustration and not as a limitation on the claimed subject matter, can be designed for functionality within a pre-specified operation set of operating parameters, such as an operating temperature range (e.g., −20-+50 degrees Celsius, etc.), a storage temperature range (e.g., −40-+70 degrees Celsius, etc.), an operating humidity range (e.g., 10-90 percent relative humidity, etc.), a storage humidity range (e.g., 10-95 percent relative humidity, etc.), operation within specification up to predefined altitudes (e.g., 10,000 feet, etc.), operation within specification at pressures up to a predefined level (e.g., 1 atm., etc.). Embodiments can also accommodate additional and/or alternative limits, ranges, and/or operating parameters consistent with the claimed subject matter.

In one embodiment, patient contact surfaces can be latex free, comfortable to the touch when contacting the patient (e.g., reduce use of metal and/or other cold contact surfaces), and/or easily cleaned and sanitized (e.g., with isopropyl alcohol and/or other material). A variety of commercially or industrially available nonmetallic materials such as polymer materials and/or engineering resin materials can be selected and used in the construction of an embodiment because they exhibit these desirable performance characteristics. For example, in one embodiment the casing of a chest piece can be made of an engineering resin equivalent to polycarbonate ABS or ABS. As another example, a diaphragm embodiment of a chest piece contact surface can be constructed of an engineering resin such as polycarbonate or glass filled nylon, listed here by way of example only, and not by way of limitation. Accordingly, even if a steel drum is provisioned under the diaphragm to help capture and resonate sound, implementing the engineering resin material on the contact surface of the diaphragm allows the chest piece to exhibit improved comfort for subjects being examined.

For reliability and quality control in operating conditions, embodiments can include an alarm or other indicator for signaling when an apparatus is out of range of one or more of its intended wireless receivers. Embodiments can also include control features so that measurements are not provided under suboptimal conditions, such as low battery power, high EMI, etc., to name but a few examples. Devices consistent with the claimed subject matter can be waterproof/water resistant. An embodiment can also be durably constructed to as to resist tampering or disassembly by users, while still enabling easy manufacturing and servicing. An embodiment can be engineered so as to need reduced or no calibration during the lifetime of the device. An embodiment can also provide for personalization (e.g., such as by including a physical space to customize a device by displaying a name of the user/owner, etc.) and unique identification, for quality/control or security purposes (such as by including a serial number and/or other identifying information on the embodiment).

It should also be appreciated that an embodiment consistent with the claimed subject matter can include functionality in addition to the functions previously mentioned. For example, an embodiment can include a blood flow ultrasonic Doppler for such purposes, among others, as studying cardiac movements, arterial flow, fetal sounds, stomach, stomach, intestine, bowel and renal activity, as well as air-emboli, to represent but a few potential uses.

Consistent with the claimed subject matter, embodiments can encompass one or more devices incorporating, at least in part, substantially user-friendly designs, ergonomics, and controls. In one embodiment, a device can include multiple controls (e.g., such as buttons, switches, thumbwheels, joysticks, etc., to name but a few examples). By way of providing an illustrated example, FIG. 22A through FIG. 22D illustrate one embodiment of a chest piece 134 exhibiting multiple user input control embodiments 132a-132d. FIG. 22A also illustrates substantially ergonomic design contours in chest piece embodiment 134. For example in the portion of illustrated chest piece embodiment 134 where user input control 132d is provisioned, a surface portion can be undercut to improve the comfort and secure grip of a hand hold on chest piece embodiment 134.

Consistent with the claimed subject matter, an embodiment can encompass one or more controls that can be provided for turning power on/off, increasing/decreasing volume, selecting an operating mode (e.g., lung, heart, or combination examination, etc.), activating/deactivating a speaker, and/or controlling wireless or other electronic communication and/or data transmission, as well as other purposes. An alternate embodiment can integrate multiple types of controls, and thus implement varied functionality, through a single and/or integrated combination control using press-and-hold, multi-press, or alternative operation. Another embodiment can use on-board processing ability to identify and diagnose specific heart, lung, and/or other sounds and present information to a user. Such an embodiment can provide an improved ability for automatic diagnosis.

Embodiments can also include multiple displays. Embodiments can include on-board displays such as, for example, LEDs, LCDs, to name but a few. On-board displays, or displays wirelessly linked to a measurement/examination device, can provide information including one or more indications of battery state, operating mode, volume level, pulse value, and/or QRS information (which can be presented in graphical form), among others. In alternate embodiments, multiple indicators can be integrated into one or more combined displays using, for example and without limitation, LCDs and/or multi-color LEDs employing either steady or flashing illumination states.

Figure 23:
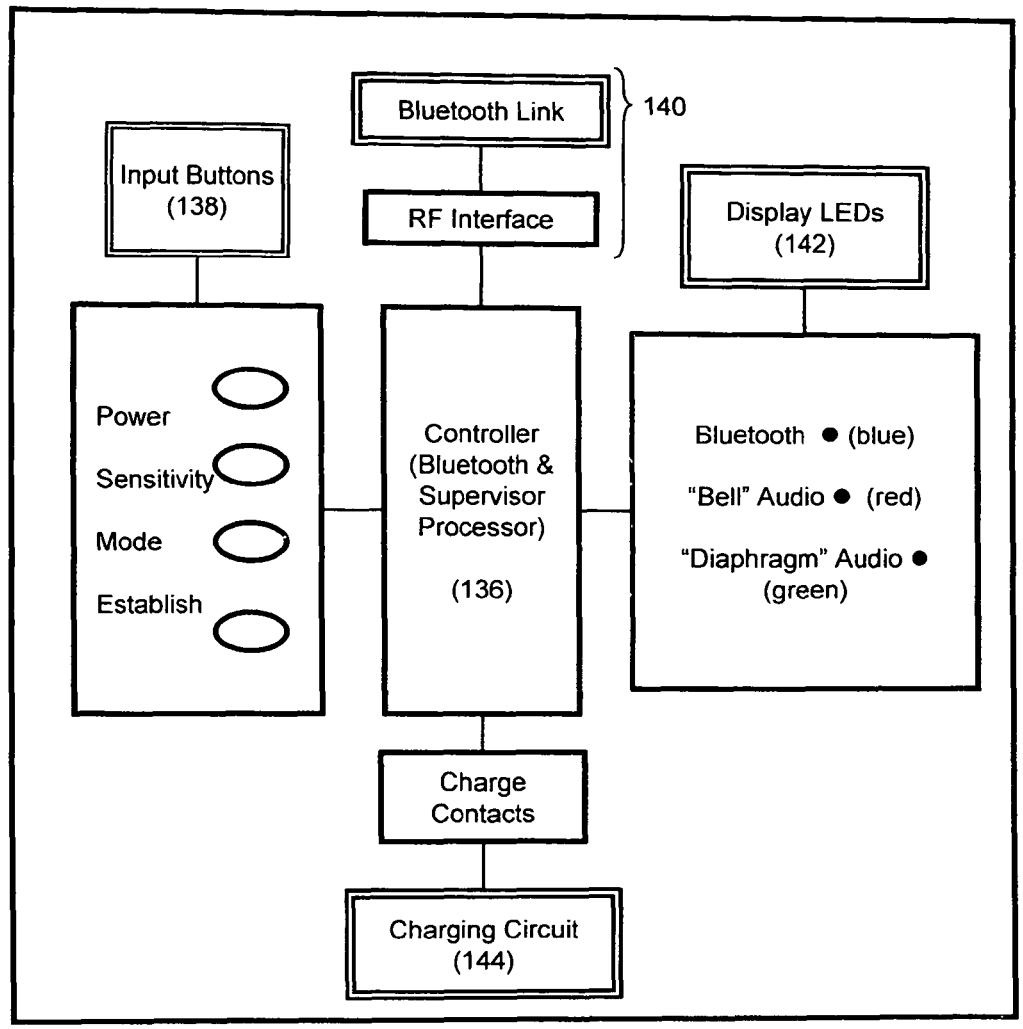
FIG. 23 illustrates a block diagram of an auscultation device having multiple interfaces, consistent with one embodiment of the claimed subject matter.

FIG. 23 illustrates a user interface block diagram of one embodiment consistent with the claimed subject matter. In the embodiment of FIG. 23, multiple physical interfaces are shown for allowing a user to interact with a device. Interface embodiments can, in part, select and/or adjust various features and/or states of a embodied device. As but a few examples presented for illustration, and not by way of limitation, interfaces can be embodied as input buttons 138 to control various features of a device, display elements 142 (e.g., LEDs, LCD, etc.) capable of displaying current status and/or other information related to a device, a wireless interface, such as a link to a Bluetooth antenna and/or other RF interface to enable connection to one or more other devices, and a charging circuit interface 144 employing electrical contacts to connect an external power source to a device. Consistent with the claimed subject matter, a controller embodiment 136, such as a Bluetooth and supervisor processor, for example, can be employed by a device to manage the various available interfaces.

One or more embodiments can enhance the user experience by offering a variety of advantageous features. For example, embodiments can provide features for, without limitation, power, listening, sensitivity, mode, wireless connection, wireless role, wireless pairing, and/or battery/power aspects of apparatuses, systems, and/or devices embodying the claimed subject matter. Embodiments described herein can include wireless functionality employing one or more Bluetooth specification standards, as well as additional and/or alternate wireless specifications, now know or later developed.

In one embodiment of a battery/power feature, an embodiment of a device can be in one of two power states: on or off. This state can be controlled by a power input button input button or through an automatic power off feature. To turn the device on, the user can press the power button. One or both of the mode LED(s) can be lit to signal to the user that the device is in a power-on state. To turn the device off, a user can press and hold the power button for a predetermined number of seconds. Any existing feature or function currently in use can be cancelled and/or terminated to complete the power-off function. When the power is off, all LEDs can remain off. This state can also be entered through an empty-battery-feature state. An automatic power-off feature can be provided so that the device automatically turns off after a predetermine number of minutes, or in response to some other predetermined status, such as a device malfunction. This can help the device reduce power consumption. In an alternate embodiment, a device can provide for an extended-power-on feature to facilitate prolonged use. For example, if the automatic power-off feature is programmed to turn the device off after a set number of seconds, pressing the power button while the device is powered on can reset the counter for the power-off feature. Such a feature can help allow the user to extend the listening feature.

One embodiment of a Listening feature can help provide for detection, amplification, and transmission of one or more audio tones originating in the body of a human or other patient. One embodiment of a device can alternate between listening states. For example, a embodiment can be in an active state if it's power is on and the Bluetooth or other connection feature is in a connected state. An active state may be visually represented by through one or more displays on the device, such as by illuminating a connection LED and one or more mode LED(s), as but one example. In the active state, the embodiment can transmit audio tones to one or more end-user listening devices or receivers. Alternatively, an embodiment may be in an idle state when the power is on and the connection feature is in a disconnected state. A disconnected state can be visually communicated to the user through one or more display functions, such as by not illuminating a connection LED but illuminating one or more mode LEDs, for example. In an idle state, an embodiment can forgo transmission of audio tones.

One embodiment of a sensitivity feature can allow the user to change the gain of the input audio circuitry. An embodiment can employ a preset and/or predefined range of acceptable values, and a default sensitivity can be defined as residing approximately in the middle of the range values or at some other predefined value. In one embodiment, a user can change the sensitivity of a device by selecting a predetermined control, e.g., by pressing a select button, etc. Multiple controls can be included to adjust sensitivity levels, or a single control can be used. As one example of a single-control embodiment, each press of a button or other control by the user can increase the sensitivity one increment toward a maximum value. When the maximum sensitivity and/or volume is reached, a subsequent press of the control can return the sensitivity level to its minimum value. An embodiment can evidence sensitivity levels though audible tones or other methods. Change it sensitivity does not have to be indicated through one or more visual displays; however, such displays may be include in alternate embodiments as such modifications are equally consistent with the claimed subject matter.

One embodiment of a mode feature can, at least in part, help a user to tailor an audio processing mode of a device, depending on the needs of the desired diagnosis. Three examples of modes can include "bell," "diaphragm," or "wide." Bell mode, for example, can transmit audio frequencies for the audio tones used for heart sounds. Diaphragm mode, for example, can transmit audio frequencies suited for the audio tones used for lung sounds. A wide mode can be defined to encompass both bell and diaphragm modes. A user can press a mode button or other control until the embodiment is active in a desired mode. Mode status can be indicated through use of a common display, such as a multi-color LED with a different being used to represent each mode. Alternatively, a separate LED or other display can be provided to represent each mode, with the embodiment alternating between activation of the alternate displays, depending on the mode of the device as selected by the user (e.g., a user can press a mode button until a "bell" indicator LED is illuminated, etc.). To help simplify the design of embodiments of the claimed subject matter, at least in part, displays such as indicator LEDs showing the mode state of a device can also provide additional information, such as conveying the power state of the device (e.g., "bell" and "diaphragm" LEDs can also indicate the current states of the Power and Battery features, etc.) When an embodiment first powers up, it can be programmed to enter a default mode, such as bell mode for example.

Consistent with the claimed subject matter, one embodiment of a Bluetooth or other connection feature can facilitate transmission of audio tones to the end user device. In one embodiment, a Bluetooth connection feature can exist in varying states. As two examples, the connection feature can be connected or disconnected. A "connected" Bluetooth connection can be active when a device is turned on and it has an active communication connection. A connection LED can be illuminated once a connection has been created. Alternately, a "disconnected" Bluetooth connection state can be active when a device is turned on and no connection exists, which, in one embodiment, can be a result of the states of the Bluetooth role and Bluetooth pairing features describe below. In a disconnected state, a connection LED can remain off.

One embodiment of a Bluetooth role feature can help allow a device to assume one or more specific roles during connection establishment. For example, a Bluetooth role can be in an "initiator" or "acceptor" state, in addition to other states that can be defined for role assignment. The initiator of the Bluetooth connection starts the connection establishment. An embodiment in an initiator state can be programmed to create a connection with its one or more paired devices automatically when the power is supplied. If the device is unpaired, it can forgo creating a Bluetooth connection. In the initiator state embodiment, a device can function as a master (in a master-slave context). In the "acceptor" state, the Bluetooth connection feature can wait until another device initiates the establishment of a connection. If the device is unpaired, it can again forgo creating and/or allowing a connection. In the acceptor state embodiment, a device can function as a slave. To change the Bluetooth role state, the user can press and release the establish button and/or operate an alternate control interface. For example, a user can press and release the specific control button to set the initiator state. In one embodiment the absence of a button press for a predetermined amount of time can set the acceptor state. For effective communications and/or data integrity, embodiments can limit the user from substantially changing the Bluetooth role feature while engaged in active listening with the device. An alternate embodiment can provide a chest piece embodiment, for example, as well as one or more additional and/or alternate system components, which can function in a master and slave role substantially simultaneously. For example, one embodiment may include a tablet computer embodiment that can function as a mater to a chest piece embodiment slave, while the chest piece embodiment can substantially simultaneously be functioning as a master to a headphone receiver embodiment slave, as but one example.

An embodiment of "Bluetooth pairing" can include the process of forming a persistent relationship between two Bluetooth devices. This can allow a device to form a connection with a paired device with reduced user interaction. Bluetooth pairing typically occurs at least once between the examination/measuring device and the end user device listening device or receiver. Embodiments can also allow Bluetooth pairing to re-occur as desired. In one embodiment, Bluetooth pairing can exist in different states. For example a device can be in a "paired" state once the pairing procedure is successfully completed. A user-friendly procedure can be followed to pair devices. For example, in one embodiment, a user can pair a device by turning on the device, pressing and holding an "establish" button for a set amount of time, and then releasing the establish button, initiating the pairing procedure on the end user Bluetooth device; pressing and releasing the establish button on the measuring device, and pressing the appropriate button on the end user Bluetooth device. Of course, the claimed subject matter is not limited in this regard, and additional or alternate steps can be included for effecting the pairing. Visual confirmation of a successful pairing can be communicated to the user through operation of one or more display elements, such as causing one or more LEDs to blink slowly, for example. An embodiment may remain in an unpaired state if the device has not been paired or if the pairing procedure failed.

A battery providing power to a device in one embodiment can also encompass multiple possible states. For example a battery can be in "normal operation" if it is ready to use. This state can be achieved when an external power source is disconnected from charge contacts on the embodiment. One or more LED(s) or other display elements can be lit or activated to signify the normal operation state. A embodiment can also enter a "charging" state when charge contacts are connected to an external power source. As one example of a visual indicator of this state, one or more LEDs can be caused to blink slowly while the device is charging, as but one example. The illuminated LEDs can also exhibit constant illumination (i.e., non-blinking) when the battery is fully charged. Use of a device can be prohibited or limited while the device is charging. A "low battery" state can also be visually indicated. For example, one embodiment can employ one or more slowly blinking LEDs to convey the low battery state. An embodiment can enter the low battery state when a predetermined, known amount of battery power remains, thus informing a user of approximate remaining power. A battery embodiment can enter an "empty battery" state when the battery's energy has been drained to a specified level. An embodiment can indicate this condition to the user by a omitting a response to button selection, as well as presenting no illuminated or active displays. In the empty battery state, the primary option available to the user is to charge the battery.

Those having skill in the art will recognize that many changes may be made to the details of the above-described embodiments without departing from the underlying principles of the invention. The scope of the present invention should, therefore, be determined only with reference to the claimed subject matter.

The invention claimed is:

1. An auscultation device, comprising:
  (a) a chest-piece ergonomically shaped for single hand operation having a nonmetallic contact surface to be placed in contact with a subject, a microphone built into said chest-piece for detecting sound from said subject and converting said sound into an electrical signal, a plurality of frequency selective band-pass analog filters built into said chest-piece to eliminate ambient noise and emphasize bell sounds, diaphragm sounds, and a combination of bell and diaphragm sounds of said electrical signal depending on an operation mode resulting in an enhanced electrical signal, a controller build into said chest-piece for electrically controlling said chest-piece, operation mode selection means for selecting said operation mode, a wireless transmitter built into said chest-piece for wirelessly transmitting said enhanced electrical signal to a wireless receiver, a battery-based power source, and a status display built into said chest-piece for displaying information including one or more indications of said operation mode, said wireless transmitter, and said battery-based power source; and
  (b) a wireless receiver piece for examination of said enhanced electrical signal, said wireless receiver piece comprising a built-in wireless receiver and a power source.

2. An auscultation device according to claim 1, wherein said controller is a microprocessor for further processing said enhanced electrical signal and controlling said auscultation device.

3. An auscultation device according to claim 1, wherein said wireless receiver piece is a hearing aid.

4. An auscultation device according to claim 1, wherein said wireless receiver includes means for storing, visually displaying, processing, and analyzing said enhanced electrical signal.

5. An auscultation device according to claim 1, wherein said nonmetallic contact surface is a latex-free nonmetallic engineering resin material.

6. An auscultation device according to claim 1, wherein said chest piece ergonomically shaped for single hand operation is ergonomically shaped as to enable a user to hold said chest piece for auscultation and selecting said operation mode using a single hand.

* * * * *